United States Patent [19]

Veerme et al.

[11] Patent Number: 4,603,050
[45] Date of Patent: Jul. 29, 1986

[54] METHOD FOR MEDICAL TREATMENT OF BONE TISSUE DEFECTS

[75] Inventors: Khelgi S. Veerme, Tallin; Arnold I. Seppo, deceased, late of Tallin, both of U.S.S.R., by Khilya K. Seppo, Kheili A. Seppo, Tynis A. Seppo, administrators

[73] Assignee: Nauchno-Issledovatelskaya Laboratoria Metalloosteosinteza S Klinikoi Imeni A, Seppo, Tallin, U.S.S.R.

[21] Appl. No.: 662,810

[22] Filed: Oct. 22, 1984

Related U.S. Application Data

[63] Continuation-in-part of Ser. No. 384,513, Jun. 3, 1982, abandoned.

[30] Foreign Application Priority Data

May 28, 1981 [SU] U.S.S.R. ............... 3282152

[51] Int. Cl.$^4$ ............ A61K 33/42; A61K 33/14; A61K 33/08; A61K 31/70
[52] U.S. Cl. ............ 424/128; 424/153; 424/157; 514/37; 514/40; 514/200
[58] Field of Search ............ 424/128, 153, 157

[56] References Cited

U.S. PATENT DOCUMENTS

| | | | |
|---|---|---|---|
| 1,086,339 | 2/1914 | Maignen | 424/157 |
| 1,225,362 | 5/1917 | Ruthrauff | 424/153 |
| 2,967,802 | 1/1961 | Towey et al. | 424/128 |
| 3,075,880 | 1/1963 | Roth | 424/128 |
| 3,238,100 | 3/1966 | Meyer et al. | 424/128 |
| 3,287,219 | 11/1966 | Nemanick | 424/153 |
| 3,417,179 | 12/1968 | Roth | 424/128 |

FOREIGN PATENT DOCUMENTS 858839 9/1981 U.S.S.R. .

OTHER PUBLICATIONS

Sultanbaev, "Acute Hematogenous Ostemoyelitis in Children", Kazakhstan Publishing House, pp. 40-41, 45-50, 80, Alma-Ata, 1979.
Ocampo Eguren, A. E., "Experimental Study of the Effect on the Pulp and . . . Calcium Hydroxide", Odontologia (Lima), vol. 13, pp. 65-91, 1965.
Merck, 9th Ed., 1976, Entry No. 8101.
Rosenthal, "Prednisolone and Calcium Hydroxide for Control of Pulpal Inflammation", Dental Survey, vol. 42, Jul. 1966, pp. 52-53.
903, "Local Treatment of Bone Tissue Infection by means of Gentamycin-Containing Acrylocement Globules", Acta orthop, belg, 1979, 45, No. 1, 57-68.
1260, "On the Problem of the Treatment of Acute Hematogenic and Secondary-Chronic Ostemyelitis in Children", Pillich et al., Z. Orthop., 1978, 116, No. 1, 40-46.
USSR Inventor's Certificate No. 799737.

*Primary Examiner*—Jerome D. Goldberg
*Assistant Examiner*—John M. Kilcoyne
*Attorney, Agent, or Firm*—Fleit, Jacobson, Cohn & Price

[57] ABSTRACT

The method disclosed herein is applicable in traumatology for treatment of infected false joints, as well as some forms of osteomyelitis.

The method consists in administering medicinal solutions to at least two areas in the locus of infection of the bone tissue, one of said solutions Medicinal Solution No. 1 having the following weight percentage composition:

| | |
|---|---|
| monobasic calcium phosphate $Ca(H_2PO_4)_2 \cdot H_2O$ | 0.0375 to 0.15 |
| calcium chloride $CaCl_2$ | 0.05 to 0.2 |
| calcium hydroxide | 1.5 to 6.0 |
| novocain | 0.09 to 0.36 |
| sodium chloride | 0.216 to 0.864 |
| antibiotic | 1.65 to 6.6 |
| water | to make up 100 percent, | the pH value of said solution being within 6.0 and 6.4, while administered to the other area of said locus of infection is an antiseptic having the pH value within 7.5 and 8.1, both of said solutions being administered dripwise continuously for 5 to 14 days per treatment course. Applied as an antibiotic is a streptomycin-calcium chloride complex, and as an antiseptic, Saluzid, Solution No. 2.

In the most preferable embodiment of the present invention the medicinal solutions are administered to the bone tissue locus of infection through the needles of the Seppo's construction.

6 Claims, No Drawings

METHOD FOR MEDICAL TREATMENT OF BONE TISSUE DEFECTS

This application is a continuation-in-part of application Ser. No. 384,513, filed June 3, 1982, now abandoned.

This invention relates generally to medicine and is concerned more specifically with a method for medical treatment of bone tissue defects.

This invention can find most efficient application in traumatology for treatment of infected false joints, and some forms of osteomyelitis.

Research has demonstrated the osseous tissue consists of organic matter (30 percent), mineral components (60 percent) and water (10 percent). The osseous organic matter is known to consist of collagen (95 percent), while as little as 5 percent accounts for other compounds. The mineral constituent of a bone is in effect the crystals of hydroxyapatite whose elementary cell can be represented as the formula $Ca_{10}(PO_4)_6(OH)_2$. This compound features such a structure that it is liable to easily give ions to the surrounding tissue fluids and to absorb these therefrom.

Healing of bone lesions is one of the inherent properties of a living organism, while the regenerative potency of the bone tissue is practically limitless. Complete and perfect reunion of bone fragments is unattainable without formation of a regenerated osseous tissue (callus) that fills up the gap between the fragments of the fractured bone. The process of reunion proceeds in several steps, i.e., first a connective layer arises round the fracture, comprising the components liable to calcify to form a callus that will turn into the bone tissue under the normal course of the fracture reunion process, which exhibits characteristic biochemical and physiological properties. However, the fractured bone is far from knitting well at any time so that false joints are liable to form at the injured spots, while the space between the bone fragments is filled up with the cartilaginous tissue on the base of which the false joint is formed. The chemical composition of such a false joint differs from that of a mineralizing cartilage in comprising the substances having high molecular weight scarcely soluble in water and hardly amenable to metabolism.

An important part is played in the regulation of the mineralization processes by mucopolysaccharides (chondroitin-sulphate and hyaluronic acid) the quantitative and qualitative composition of which is to a great extent decisive for the course of the mineralization process. The aforesaid substances are capable of reacting with other biopolymers, in particular with proteins, to form the so-called protein-hydrocarbon complexes (glycoprotieds) which are no longer capable of mineralizing.

It is chondroitin-sulphate readily combinable with calcium that plays a cardinal part in the bone mineralization processes as calcium is transferred from the surrounding tissue fluid into the bone with the help of that compound. However, when chondroitin-sulphate is combined with any other substance it is no longer capable of combining and transferring calcium. Disturbed mineralization process in the case of pseudarthrosis can also be accounted for by a reduced content of chondroitin-sulphate due to an increased content of the other mucopolysaccharide, that is, hyaluronic acid. Thus, the chemical composition of the cartilaginous tissue is affected in the case of a false joint, whereby said tissue loses ability to mineralize. That is why a normal course of the mineralization processes involves an optimum ratio of the mucopolysaccharides participating in the formation of hydroxyapatite crystals as they are capable of selectively combining Ca and $PO_4$ ions.

Whenever infected false joints arise it is the pathological inflammatory process that is responsible for specific dynamic chemical changes in the tissues involved, especially at the site where the process is localized. This inflammatory locus becomes the original point of a chain of pathologic processes tha develop immediately in the neuro-humoral system and affect to a greater or lesser extent the organism as a whole.

Our research has demonstrated that:

(1) The bone tissue which exhibits a reduced Ca content is less resistant to infections. Therefore when the osseous medium is enriched with Ca until the ratio of Ca:P equals 1.66:2.0, pathogens become much less resistant to, say, streptomycin;

(2) When the pH value ranges between 6.0 and 8.0 the growth conditions for the microorganisms at the locus of infection are badly affected.

Proceeding from the above a medium should be established in the zone of the infected false joint, wherein the pathogenic microorganisms propagate but poorly and are readily amenable to the effects of antibiotics and at the same time the mineral composition of the osseous tissue should be restored artificially by changing the basic ion equilibrium to that which is reciprocal to the pathologic one, so as to provide favourable conditions for regeneration of the bone tissue.

However, when administered to the organism by any commonly adopted techniques, including an intraosseous route, antibiotics are liable to promptly get into the circulation system and to be carried to the organs and tissues of the patient's organism in proportion with the intensity of their blood supply and tropism. As it has been demonstrated by research work carried out by Tröppinger (cf. "Zur Pathogenese und Therapie der Skelett und Urogenitaltublese", Z. Tuberkul., 1956, 108, 5, pp. 257–268), with an adequate concentration of antibiotics in the blood circulating through the osseous tissue, only traces of the antibiotics administered are detectable in the osseous tissue itself. Moreover, the pH value and the Ca/P ion concentration in the osseous tissue are even less amenable to any change as it is opposed by the blood buffer system itself.

One prior-art method for treatment of pseudarthrosis described in patent literature (cf. USSR Inventor's Certificate No. 695,663, $IPC^2$ A61B 17/00 issued on Feb. 22, 1977) is carried out by refreshing the ends of the bone fragments, forming bone transplants of different lengths from the bone fragments and displacing the transplants through the line of fracture, said bone transplants being shaped as rings at the ends of a tubular bone and then mutually relocated, while the bone fragments are reposited and fixed by means of an intramedullary fixator using any of the commonly adopted techniques.

A disadvantage inherent in said method resides in its being inapplicable in the cases of infected false joints since the use of intramedullary nails and bone transplants is inadmissible.

Another prior-art method (cf. U.S. Pat. No. 3,828,772, IPC A61f 5/00; NPC 128-92G, priority data Aug. 25, 1972) is known to describe reunion of bone fragments by injecting, using a syringe, into the zone where the bone fragments adjoin, a minimum dose of a thinned composition containing a non-necrotizing mixture of a fatty acid, a vasoconstrictor, and a fluid vehicle having the pH value of 8 to 9. Administration by injection is repeated in ten days until a complete union of the bones occurs.

However, said method suffers from the cardinal disadvantage that it is inapplicable in the cases of infected pseudarthrosis, since the method fails to provide conditions required for suppressing the locus of infection in the inflamed bone tissue and infected false joint, and for growth of the bone tissue. Furthermore the process of administering a medicinal solution under pressure (by injection) might contribute to further propagation of the infection.

It is therefore a primary object of the present invention to attain a complete curing of destructive (infected) lesions of the bone tissue such as infected pseudarthrosis with markedly pronounced destructive lesion, and also osteomyelitis.

It is another object of the present invention to stimulate regeneration of the bone tissue in the case of its being affected by infectious diseases or destructive lesions.

It is one more object of the present invention to provide medical treatment of infected false joints without applying any plaster bandage for immobilization.

And it is an additional object of the present invention to provide a sparing therapy method for treatment of infected lesions of the bone tissue.

The aforesaid and other objects are accomplished by a method for medical treatment of the bone tissue defects, consisting in administration to at least two areas within the locus of infection of the bone tissue, of medicinal solutions so that administered to one of said areas is Solution No. 1 of the following weight percentage composition:

| monobasic calcium phosphate $Ca(H_2PO_4)_2 \cdot H_2O$ | 0.0375 to 0.15 |
| calcium chloride $CaCl_2$ | 0.05 to 0.2 |
| calcium hydroxide | 1.5 to 6.0 |
| novocain | 0.09 to 0.36 |
| sodium chloride | 0.216 to 0.864 |
| antibiotic | 1.65 to 6.6 |
| water | to make up 100 percent | the pH value being within 6.0 and 6.4, whereas administered to the other area is an antiseptic having a pH value of between 7.5 and 8.1, both of the afore-mentioned solutions being administered drip wise continuously for 5 to 14 days per course of treatment.

The herein-disclosed method for medical treatment of bone tissue defects enables one to completely cure such diseases as infected pseudarthrosis, even those exhibiting markedly pronounced destructive lesion, as well as some forms of chronic osteomyelitis.

This can be achieved due to the fact that appropriate medicinal substances having the pH value ranging within 6.0 to 6.4 and 7.5 to 8.1, are administered *immediately* to the locus of infection but not syringe-injected under pressure.

It is expedient that the aforesaid areas of the bone tissue locus of infection be spaced 5 to 30 mm apart from each other.

Such limits have been selected because the medicinal preparations administered to said areas should react chemically with each other. As our studies have demonstrated the maximum effect is attained when the medicinal substances are administered to the areas spaced apart within the afore-stated limits.

It is quite reasonable that a streptomycin-calcium chloride complex be applied as an antibiotic.

The expediency of applying said complex is due to the $CaCl_2$ content of said complex, which in fact is the nutrient mass for the growth of the bone tissue. Moreover said complex provokes no allergic complications in patients treated with it, while the majority of microbial pathogens are sensitive to its effects. Although a streptomycin-calcium chloride complex is the preferred antibiotic, any antibiotic which has an effective impact on the microflora vegatating in a locus of infection is suitable for use in the method of the present invention. Other suitable antiobiotics are gentamycin and cephalosporines.

According to one of the embodiments of the present invention Saluzid is the antiseptic used in Solution No. 2.

In this embodiment of the method of the present invention a chemical reaction between Solution No. 2, Saluzid and the medicinal solutions administered to the interstitial fluid of the bone tissue results in precipitation, in the form of a colloid and very fine crystalline mass, of hydroxyapatite rich in Ca ions which is indispensable for artificial restoration of the mineral composition of the bone tissue.

According to another embodiment of the present invention used as an antiseptic is Solution No. 3 of the following weight percentage composition:

| boric acid $H_2BO_3$ | 2.5 to 1.5 |
| calcium hydroxide | 97.5 to 98.5 | the pH value being within 7.5 and 8.1.

The aforesaid Solution No. 3 may be used instead of Saluzid, e.g. Solution No. 2, e.g., in repeated treatment courses.

In the case of inveterate infected pseudarthrosis or in advanced-age patients the treatment course should be repeated at an interval of from 1.5 to 3 months.

In such cases the process of artificial restoration of the mineral composition of the bone tissue, that is, a change of the basic ion equilibrium which is reciprocal to the pathologic one runs at a low rate and needs therefore additional effects.

On the ground of a twenty-year practice of treating infected pseudarthrosis and osteomyelitis by the A. I. Seppo's method we have established that a repeated treatment course applied after a 1.5 to 3-month interval makes it possible to completely cure said diseases (cf. Case records Nos 1018, 2490, 2337, 665).

It is quite expedient to administer medicinal solutions to the locus of infection in the bone tissue with the use of the Seppo's needles which are known per se.

Application of the Seppo's needles for administering medicinal solutions to the locus of infection of the bone tissue is instrumental to the most efficient realization of the proposed method, and renders said method most sparing as compared to any of the heretofore known methods because administration with said needles inflicts little trauma, while the process of administration itself runs painlessly and needs no needle replacement throughout the treatment course. In addition, application of such needles makes it possible in a majority of cases to dispense with the use of a plaster bandage for immobilization.

Other objects and advantageous features of the present invention will become apparent from a detailed description of some embodiments thereof that hereinafter follow.

Infected pseudarthrosis and chronic posttraumatic osteomyelitis are liable to result in formation of loci of infection into which neither the circulating blood nor medicinal substances can penetrate. Thus, an avascular zone sets up round the osteomyelitic locus. Parenteral administration of antibiotics (intramuscular or intravenous) can produce an ameliorative effect upon the general course of the disease in the case of purulent osteitis but is incapable of producing an adequate therapeutic effect sufficient to stop the suppurative infection nor can it prevent further destructive lesion of the bone involved.

We have developed a method for continuous long-term intraosseous administration of medicinal solutions using therapeutic needles of the A. I. Seppo's construction (cf. USSR Inventor's Certificate No. 858,839).

A needle of said construction comprises a body, a tubular needle and a union, both being held to the body and separably connected to a container with the medicinal solution to be administered. The body accommodates a pivotally mounted mandrin provided with a tapered plug and a handle. A gasketed nut closes tightly the body with the tubular needle and the mandrin with the tapered plug accommodated therein.

The therapeutic needle is brought into the bone as follows. The exterior surface of the extremity within the region of the false joints is disinfected with a 5-percent iodinate solution. Then the area of application of the needle is subjected to toponarcosis with a 0.5-percent trimecaine solution, and the mandrin of the sterilized needle is replaced by a burr, and the burr head is held in the burrdrill, whereby the needle is introduced into the false joint or the bone destruction locus. Next the burr is extracted and changed for the mandrin, and the therapeutic needle is tightly closed by the plug with a rubber gasket.

Two needles are introduced as a rule on the areas at the bone tissue locus of infection on the exterior surface of the extremity, said areas being spaced 5 to 30 mm apart.

Infected false joints without markedly pronounced sequestra are to be subjected to conservative treatment only as follows. First the infection is suppressed by a course of antibiotic medication applied through the surgical needles of the A. I. Seppo's construction, whereupon, with a view to stimulating regeneration of the bone tissue and filling up the false joint cavity, medicinal Solution No. 1 is administered through one of the surgical needles, said Solution No. 1 having the following weight percentage composition:

| monobasic calcium phosphate $Ca(H_2PO_4)_2.H_2O$ | 0.0375 to 0.15 |
| calcium chloride $CaCl_2$ | 0.05 to 0.2 |
| calcium hydroxide | 1.5 to 6.0 |
| novocain | 0.09 to 0.36 |
| sodium chloride | 0.216 to 0.864 |
| antibiotic | 1.65 to 6.6 |
| water | to make up 100 percent, | the pH value being within 6.0 and 6.4, whereas administered through the other needle is an antiseptic having a pH value within 7.5 and 8.1, both of the aforesaid solutions being administered dripwise continuously for as long a period as 5 to 14 days per course of treatment.

Used as an antibiotic may be a streptomycin-calcium chloride complex, and as an antiseptic, Saluzid, Solution No. 2. Administered through the other needle may also be Solution No. 3 of the following weight percentage composition (pH=7.5 to 8.1):

| boric acid $H_2BO_3$ | 2.5 to 1.5 |
| calcium hydroxide | 97.5 to 98.5. |

The rate of dripwise feed of the medicinal solutions is regulated, by turning the mandrin handle, to be within 20 to 30 drops per minute.

The medicinal solutions thus administered impregnate the bone tissue to get mixed with the interstitial fluid thereof and enter into reaction with the latter, with the result that hydroxyapatite rich in Ca ions precipitates in the form of a colloid and very fine crystalline mass, and a jelly-like matter is discharged outwards. The vials containing the medicinal solutions are changed twice a day.

No immobilization of the extremity being treated is needed in a majority of cases through an extraordinary cases where badly pathological mobility of the false joint is observed, resort can be made to a posterior plaster splint or skeletal traction which is the case with, say, fractured femoral bone. The treatment course lasts from 5 to 15 days.

In cases of inveterate infected pseudarthrosis or when advanced-age patients are involved the treatment course is to be repeated at an interval of from 1.5 to 3 months.

Infected pseudarthrosis without explicitly defined sequestra are curable completely and comprehensively.

Destructive forms of infected pseudarthrosis exhibiting markedly pronounced sequestra are first subjected to surgical treatment according to a commonly adopted technique, then to the therapy by the proposed method.

Whenever necessary the treatment course can be repeated at an interval of from 1.5 to 3 months.

Infected pseudarthrosis with markedly pronounced sequestra are likewise curable without exception.

With the splinters of the fractured bone spaced wider than 30 mm apart use may be made of three or more needles at a time, while the administration of the medicinal solution into the injured bone is carried out by the same technique.

The herein-disclosed method of treatment has been subjected to trial under clinical conditions. Given below are a number of case records to cite.

Patient Raudkivi Yu., aged 33 (Case record No. 1018, dated February, 1978).

Diagnosis: chronic osteomyelitis accompanied by pseudarthrosis of the right femoral bone after a comminuted fracture and intramedullary metalloosteosynthesis with purulent discharge.

On Nov. 18, 1977 the patient was involved in a road accident, whereby he suffered a closed comminuted fracture of the right femoral bone accompanied by bruising of the soft tissues.

Treatment before admission: Intramedullary nailing osteosynthesis has been carried out; three weeks later the nail has been removed on account of infection. The patient has been given skeletal traction; a plaster bandage has been applied. As a result the infection locus and pathologic mobility of the bone fragments have persisted. *Staphylococcus pyrogenes aureus* has been isolated from the purulent discharge.

Treatment after admission: The patient has been given two courses of intraosseous treatment with antibiotics effective against the given staphylococcus and administered immediately to the locus of infection through the therapeutic needles of the A. I. Seppo's construction, followed by a ten-day course of treatment with No. 1 and No. 2 medicinal solutions. As a result, purulent discharge has ceased. The patient has started walking with crutches, four months later, with a single crutch only, while in half a year the fracture has been completely consolidated.

Patient Istomin Yu., aged 26 (Case record No. 2490, dated Apr. 10, 1978).

Diagnosis: Chronic osteomyelitis in combination with pseudarthrosis of the upper third of the tibial bone resulted from an open comminuted fracture of that bone and intramedullary metalloosteosynthesis with two suppurative fistulas.

On July 29, 1977 the patient, being a victim of a road accident, suffered from an open comminuted fracture of the left tibial bone.

Treatment before admission: Skeletal traction and intramedullary nailing metalloosteosynthesis have been performed. Once infection has set in, the nail has been removed and a plaster bandage has been applied. However, the fractured bone has failed to consolidate and infection has persisted. The causative agent of the infection has been identified as *Staphylococcus pyrogenes aureus*.

Treatment after admission: Treatment has been applied with the use of A. I. Seppo's therapeutic needles. First a course of antibiotic therapy has been carried out, then two courses (seven- and six-day ones) have been given using No. 1 and No. 2 medicinal solutions at a 1.5-month interval therebetween. As a result, the fistulas have closed, pathologic mobility of the bone fragments has decreased. Three months later the patient has been permitted to partially rest upon the affected leg, while in five months a complete support by the affected leg has been allowed. The fracture has become consolidated completely.

Patient Allik R., aged 37 (Case record No. 2337, dated Apr. 4, 1978).

Diagnosis: Chronic osteomyelitis against the background of a retarded knitting of the right tibial bone after an open fracture. A suppurative fistula in the area of the shin.

In March, 1976 the patient was knocked down by a car and sustained an open fracture of the right crural bones.

Treatment before admission: A plaster bandage has been applied, though the fractured tibial bone has failed to exhibit reunion.

Treatment after admission: On Feb. 20, 1977 metalloosteosynthesis was applied with the use of the A. I. Seppo's reponator-fixator. However, infection has set in and the process of reunion has been sluggish. A therapy course has been given for ten days with antibiotics, and another course (eight days) with No. 1 and No. 2 solutions, using the A. I. Seppo's therapeutic needles. As a result, purulent discharge has stopped.

Four months later (Case record No. 4884, dated Aug. 26, 1978) the reponator-fixator has been removed and one more therapy course (five days) has been given with No. 1 and No. 3 solutions administered through the therapeutic needles.

A complete reunion has occurred in five months as evidenced by X-ray photographs.

Patient Kozyrev V, aged 41 (Case record No. 665, 1980).

Diagnosis: Chronic posttraumatic osteomyelitis in combination with psueodarthrosis of the left tibial bone. A suppurative fistula is observed.

In 1964 the patient sustained a fracture of the left crural bones. Metalloosteosynthesis with the A. I. Seppo's reponator-fixator has been applied, whereupon the fractured bones have knitted and the reponator-fixator has been removed. The patient has been able to resume to his previous occupation, i.e., a sailor.

In 1979 the patient sustained a blow delivered to the region of the formerly fractured bone. Thus, infection has set in followed by the bone destruction. A false joint has formed in the area of the former fracture.

Treatment after admission: The surgery for necrectomy has been followed by a six-day course of therapy with No. 1 and No. 2 solutions. Nevertheless the fistula has remained open. Four months later a repeated treatment course has been carried out for removal of the newly set up sequestra and seven-day therapy course with No. 1 and No. 3 solutions, whereupon the fistula has been closed. Four months later the patient has been allowed to rest partially upon his left leg, while in seven months a complete consolidation of the fracture has occurred.

Patient Freirich Yu., aged 19 (Case record No. 502, dated Mar. 23, 1981).

Diagnosis: Chronic osteomyelitis in combination with pseudarthrosis of the left tibial bone as a result of an open fracture and intramedullary metalloosteosynthesis application. A suppurative fistula of the left shin.

In the spring of 1980 the patient was involved in a traffic accident with his motorcycle, whereby he sustained an open comminuted fracture of the left crural bones.

Treatment before admission: There has been applied intramedullary nailing metalloosterosynthesis. Since infection has set up the nail has been removed through purulent discharge has persisted. The pathogen has been recognized as *Staphylococcus pyogenes aureus*.

Treatment after admission: A radical operation for osteomyelitis has been performed. An antibiotic therapy course has been followed by a nine-day course of treatment with No. 1 and No. 2 administered through the A. I. Seppo's therapeutic needles. Status before dismissal from the hospital: purulent discharge from the fistula has stopped. Pathological mobility has become minimal. Four months later (in September) the patient has come for control examination leaning upon a walking-stick. As it has been evidenced by X-ray photographs the fractured bones were knitted.

Patient Kovshunov A., aged 54 (Case record No. 255, dated Feb. 12, 1981).

Diagnosis: Chronic osteomyelitis in conjunction with pseudarthrosis of the right femoral bone as a result of an open fracture and application of intramedullary metalloosteosynthesis.

In October, 1980 the patient was knocked down by a car, whereby he sustained an open displaced fracture of the right femoral bone.

Treatment before admission: Skeletal traction and intramedullary metalloosteosynthesis have been effected. Since infection has set in the nail has been removed.

Treatment after admission: A radical operation for osteomyelitis has been performed followed by skeletal traction applied for two months. A twelve-day course of treatment with No. 1 and No. 2 solutions has been performed through the use of the therapeutic needles. Three months later the patient has begun walking with crutches and at the same time consolidation of the fractured bone has been detected by X-ray photographing.

Patient Piyrsalu B., aged 56 (Case record No. 700, dated Apr. 27, 1981).

Diagnosis: Chronic osteomyelitis against the background of a retarded knitting of the left femoral bone after an open comminuted displaced fracture followed by treatment with metalloosteosynthesis.

On Feb. 25, 1981 a heavy metal sheet dropped on the left thigh of the patient and inflicted an open comminuted displaced fractured upon the femoral bone.

Treatment before admission: Metalloosteosynthesis has been applied using a plate and woodscrews. Infection has set in, and callus formation has been retarded.

Treatment after admission: Once the metallic plate has been removed skeletal traction has been applied within a 1.5-month period. Then a ten-day course of treatment with antibiotics administered through the therapeutic needles has been given, followed by another ten-day course of treatment with No. 1 and No. 2 solutions. In 2.5 months the patient has begun walking with crutches without loading the affected leg. Control examination carried out one month later has revealed further strengthening of the callus; the patient has been permitted to walk while partially loading the affected leg.

Patient Peshiy V., aged 27 (Case record No. 1654, dated on Oct. 16, 1981).

Diagnosis: Exacerbated chronic hematogenic osteomyelitis of the proximal metaphysis of the right tibial bone. Suppurative fistula in the right shin.

Since 1968 the patient has suffered from hematogenic osteomyelitis of the right tibial bone and has been subjected to repeated surgical and conservative treatment at various medical institutions. Notwithstanding only transitory closure of the fistula has occurred.

Treatment after admission: A course of intraosseous administration of antibiotics using the A. I. Seppo therapeutic needles has been carried out until purulent discharge from the fistula has ceased, whereupon another course of treatment with No. 1 and No. 2 solutions has been performed to fill up the osteomyeolitic cavern. As a result, the fistula has closed. Two months later the patient has made no complaints. As evidenced by an X-ray photograph the bone structure is shown to normalize within the region of the proximal metaphysis of the right tibial bone.

What we claim is:

1. A method for medical treatment of bone tissue defects, in a patient, selected from the group consisting of osteomyelitis and infected pseudarthrosis, comprising administering two different solutions to at least two areas in the locus of infection of the bone tissue, one of said solutions administered to one of said areas being a medicinal Solution No. 1 having the following weight percentage composition:

| | |
|---|---|
| monobasic calcium phosphate $Ca(H_2PO_4)_2.H_2O$ | 0.0375 to 0.15 |
| calcium chloride $CaCl_2$ | 0.05 to 0.2 |
| calcium hydroxide | 1.5 to 6.0 |
| novocain | 0.09 to 0.36 |
| sodium chloride | 0.216 to 0.864 |
| an antibiotic selected from the group consisting of a streptomycin-calcium chloride complex, gentamycin and cephalosporines | 1.65 to 6.6 |
| water | to make up 100 percent, | the pH value being within 6.0 and 6.4, while administered to at least one other area in said locus of infection an antiseptic solution having the pH value within the range of 7.5 to 8.1 and selected from the group consisting of Saluzid designated, Solution No. 2, and a solution containing 1.5 to 2.5% by weight of boric acid and 97.5 to 98.5% by weight of calcium hydroxide, designated Solution No. 3, said Solution Nos. 1 and one of Solutions Nos. 2 or 3 being administered dripwise continuously for 5 to 14 days at the rate of between about 20 to 30 drips per minute to said patient.

2. A method for medical treatment of bone tissue defects as claimed in claim 1, wherein said at least two areas in the bone tissue locus of infection are spaced 5 to 30 mm apart from each other.

3. A method for medical treatment of bone tissue defects as claimed in claim 1, wherein said antibiotic is a streptomycin-calcium chloride complex.

4. A method for medical treatment of bone tissue defects as claimed in claim 1, wherein said antiseptic is Saluzid.

5. A method for medical treatment of bone tissue defects as claimed in claim 1, wherein said dripwise administration of said solutions is to be repeated at an interval of from 1.5 to 3 months.

6. A method for medical treatment of bone tissue defects as claimed in claim 1, wherein said administration of the medicinal solution and the antiseptic solution to the locus of infection is carried out with Seppo's needles.

* * * * *